(12) United States Patent
Smith et al.

(10) Patent No.: US 10,209,258 B2
(45) Date of Patent: Feb. 19, 2019

(54) LIPOPROTEIN NANOPLATELETS: FLUORESCENT, ZWITTERIONIC PROBES FOR MOLECULAR AND CELLULAR IMAGING

(71) Applicant: The Board of Trustees of the University of Illinois, Urbana, IL (US)

(72) Inventors: Andrew Smith, Savoy, IL (US); Sung Jun Lim, Champaign, IL (US); Aditi Das, Champaign, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 136 days.

(21) Appl. No.: 15/244,026

(22) Filed: Aug. 23, 2016

(65) Prior Publication Data

US 2017/0059575 A1    Mar. 2, 2017

Related U.S. Application Data

(60) Provisional application No. 62/209,257, filed on Aug. 24, 2015.

(51) Int. Cl.
*A61K 49/00* (2006.01)
*G01N 33/50* (2006.01)
*G01N 33/58* (2006.01)

(52) U.S. Cl.
CPC ....... *G01N 33/588* (2013.01); *A61K 49/0067* (2013.01); *G01N 33/5032* (2013.01)

(58) Field of Classification Search
CPC ............. A61K 49/0067; G01N 33/588; G01N 33/5032
See application file for complete search history.

(56) References Cited

U.S. PATENT DOCUMENTS

| | | | | |
|---|---|---|---|---|
| 8,323,686 | B2* | 12/2012 | Mirkin | A61K 9/1275 424/450 |
| 2004/0033345 | A1* | 2/2004 | Dubertret | A61K 49/0067 428/220 |
| 2011/0248222 | A1* | 10/2011 | Dubertret | B01J 13/00 252/519.4 |
| 2015/0183939 | A1* | 7/2015 | Lequeux | A61K 49/0067 436/501 |

OTHER PUBLICATIONS

Dubertret et al, Science 298:1759-1762, 2002.*
Tessier et al, Nano Letters 14:207-213, 2014; available online Dec. 11, 2013.*

(Continued)

*Primary Examiner* — Kevin K Hill
(74) *Attorney, Agent, or Firm* — Dilworth IP, LLC

(57) ABSTRACT

Compositions are provided comprising water-stable semiconductor nanoplatelets encapsulated in a hydrophilic coating further comprising lipids and lipoproteins. Uses include biomolecular imaging and sensing, and methods of making comprise: colloidal synthesis of CdSe core NPLs; layer-by-layer growth of a CdS shell; and encapsulation of CdSe/CdScore/shell NPLs in lipid and lipoprotein components through an evaporation-encapsulation using zwitterionic phospholipids, detergents, and amphipathic membrane scaffold proteins.

13 Claims, 4 Drawing Sheets

(56) References Cited

OTHER PUBLICATIONS

Mahler et al, J. Am. Chem. Soc. 134:18591-18598, 2012.*
Prudnikau et al, J. Am. Chem. Soc. 135:14476-14479, 2013.*
Kunneman et al, Nano Letters 14:7039-7045, 2014; available online Nov. 4, 2014.*
Morgan et al, Mol. Cell. Proteomics 10(9): 11 pages, 2011.*
Huda et al, PLOS One 10(7):e0129310, 14 pages, Jul. 1, 2015.*
Kairdolf, B. A. et al., "Semiconductor Quantum Dots for Bioimaging and Biodiagnostic Applications", Ann. Rev. anal. Chem. 6, 143-162 (2013).
Talapin, D. V. et al., "Prospects of Colloidal Nanocrystals for Electronic and Optoelectronic Applications", Chem. Rev. 110, 389-458 (2010).
Mashford, B. S. et al., "High-efficiency quantum-dot light-emitting devices with enhanced charge injection", Nature Photonics, vol. 7, May 2013, pp. 407-412, published online Apr. 21, 2013, Macmillan Publishers.
Pinaud, F. et al., "Probing cellular events, one quantum dot at a time", Nature Methods, vol. 7, No. 4, Apr. 2010, pp. 275-285, © 2010 Nature America, Inc.
Smith, A. M. et al., "Semiconductor Nanocrystals: Structure, Properties, and Band Gap Engineering", Acc. Chem. Res. 43, 190-200 (2010).
Lim, S. J. et al., "The more exotic shapes of semiconductor nanocrystals: emerging applications in bioimaging", Current Opinion in Chemical Engineering 2014, 4, pp. 137-143, 2014 Elsevier Ltd.
Deka, S. et al., "CdSe/CdS/ZnS Double Shell Nanorods with High Photoluminescence Efficiency and Their Exploitation As Biolabeling Probes", J. Am. Chem. Soc. 2009, 131, pp. 2948-2958, published on web Feb. 10, 2009, 2009 American Chemical Society.
Ithurria, S. et al., "Colloidal nanoplatelets with two-dimensional electronic structure", Nature Materials, vol. 10, Dec. 2011, pp. 936-941, www.nature.com, Macmillan Publishers.
Ithurria, S. et al., "Quasi 2D Colloidal CdSe Platelets with Thicknesses Controlled at the Atomic Level", J. Am. Chem. Soc. 2008, vol. 130, No. 49, pp. 16504-16505, published on Web Nov. 14, 2008, American Chemical Society.
Hyeon, T., "Large-Scale Soft Colloidal Template Synthesis of 1.4 nm Thick CdSe Nanosheets**", Angewandte Chemie Int. Ed. 2009, 48, pp. 6861-6864, Wiley-VCH Verlag GmbH & Co. KGaA, Weinheim.
Bouet, C. et al., "Two-Dimensional Growth of CdSe Nanocrystals, from Nanoplatelets to Nanosheets", Chemistry of Materials 2013, 25, pp. 639-645, published Jan. 31, 2013, ACS Publications.
Ithurria, S. et al., "Colloidal Atomic Layer Deposition (c-ALD) using Self-Limiting Reactions at Nanocrystal Surface Coupled to Phase Transfer between Polar and Nonpolar Media", J. Am. Chem. Soc. 2012, 134, pp. 18585-18590, published Oct. 12, 2012, ACS Publications.
Mahler, B. et al., "Core/Shell Colloidal Semiconductor Nanoplatelets", J. Am. Chem. Soc. 2012, 134, pp. 18591-18598, published Oct. 12, 2012, ACS Publications.
Tessier, M. D. et al., "Spectroscopy of Colloidal Semiconductor Core/Shell Nanoplatelets with High Quantum Yield", Nano Letters, 2013, 13, pp. 3321-3328, published Jun. 3, 2013, ACS Publications.
Bayburt, T. H. et al., "Self-Assembly of Discoidal Phospholipid Bilayer Nanoparticles", Nano Letters, 2002, vol. 1, No. 8, pp. 853-856, published on Web Jul. 18, 2002, American Chemical Society.
Denisov, I. G. et al., "Directed Self-Assembly of Monodisperse Phospholipid Bilayer Nanodiscs with Controlled Size", Published on Web Mar. 2, 2004J. Am. Chem. Soc. 2004, 126, 3477.
Bayburt, T. H. et al., "Membrane protein assembly into Nanodiscs", FEBS Letters 584, 2010, pp. 1721-1727, available online Oct. 16, 2009, Federation of European Biochemical Societies, Elsevier B.V.
Bayburt, T. H. et al., "Assembly of single bacteriorhodopsin trimers in bilayer nanodiscs", Archives of Biochemistry and Biophysics 450 (2006) pp. 215-222, available online Mar. 29, 2006, Elsevier Inc.

Das, A. et al., "Screening of Type I and II Drug Binding to Human Cytochrome P450-3A4 in Nanodiscs by Localized Surface Plasmon Resonance Spectroscopy", Analytical Chemistry, vol. 81, No. 10, pp. 3754-3759, May 15, 2009, American Chemical Society.
McDougle, D. R. et al., "Functional studies of N-terminally modified CYP2J2 epoxygenase in model lipid bilayers", Protein Science 2013, vol. 22, pp. 964-979, published online May 10, 2013, by Wiley-Blackwell.
Pellegrino, T. et al., "Hydrophobic Nanocrystals Coated with an Amphiphilic Polymer Shell: A General Route", Nano Letters 2004, vol. 4., No. 4, pp. 703-707, published on Web Mar. 26, 2004, ACS Publications.
Smith, A. M. et al., "Minimizing the Hydrodynamic Size of Quantum Dots with Multifunctional Multidentate Polymer Ligands", Journal of American Chemical Society, vol. 130, No. 34, 2008, pp. 11278-11279, published on Web Aug. 5, 2008, ACS Publications.
Dubertret, B. et al., "In Vivo Imaging of Quantum Dots Encapsulated in Phospholipid Micelles", Science, vol. 298, Nov. 29, 2002, pp. 1759-1762, www.sciencemag.org, American Association for the Advancement of Science.
Mulder, W. J. et al., "Quantum Dots with a Paramagnetic Coating as a Bimodal Molecular Imaging Probe", Nano Letters, vol. 6, No. 1, Jan. 2006, ACS Publications.
Cormode, D. P. et al., "Nanocrystal Core High-Density Lipoproteins: A Multimodality Contrast Agent Platform", Nano Letters 2008, vol. 8, No. 11, pp. 3715-3723, ACS Publications.
Skajaa, T. et al., "Quantum Dot and Cy5.5 Labeled Nanoparticles to Investigate Lipoprotein Biointeractions via Forster Resonance Energy Transfer", Nano Letters 2010, 10, pp. 5131-5138, ACS Publications.
McMahon, K. M. et al., "Biomimetic High Density Lipoprotein Nanoparticles for Nucleic Acid Delivery", Nano Letters, 2011, 11, pp. 1208-1214, ACS Publications.
Gopalakrishnan, G. et al., Multifunctional Lipid/Quantum Dot Hybrid Nanocontainers for Controlled Targeting of Live Cells**Angew. Chemie Int. Ed. 2006, 45, pp. 5478-5483, Wiley-VCH Verlag GmbH & KGaA, Weinheim.
Al-Jamal, W. T. et al., Lipid-Quantum Dot Bilayer Vesicles Enhance Tumor Cell Uptake and Retention in Vitro and in Vivo, ACS Nano 2008, vol. 2, No. 3, pp. 408-418, ACS Publications.
Zheng, W. et al., "Quantum Dots Encapsulated within Phospholipid Membranes: Phase-Dependent Structure, Photostability, and Site-Selective Functionalization", J. Am. Chem. Soc. 2014, 136, pp. 1992-1999 ACS Publications.
Johnsson, M., "Liposomes, Disks, and Spherical Micelles: Aggregate Structure in Mixtures of Gel Phase Phosphatidylcholines and Poly(Ethylene Glycol)-Phospholipids", Biophysical Journal, vol. 85, Dec. 2003, pp. 3839-3847, Biophysical Society.
Nagarajan, R. "Molecular Packing Parameter and Surfactant Self-Assembly: The Neglected Role of the Surfactant Tail\", Langmuir 2002, vol. 18, No. 1 pp. 31-38, ACS Publications.
Arnspang, E. C. et al., "Multi-Color Single Particle Tracking with Quantum Dots", PLoS One, Nov. 2012, vol. 7, Issue 11, e48521, 12 pages.
Jasieniak, J. et al., "Re-examination of the Size-Dependent Absorption Properties of CdSe Quantum Dots", J. Phys. Chem. C 2009, 113, pp. 19468-19474, ACS Publications.
Smith, A. M. et al., "Quantum dots that are small and non-blinking offer new opportunities for dynamic single-molecule imaging in live cells.", Nature Biotechnology, vol. 27, No. 8, Aug. 2009, pp. 732-733, Nature America, Inc.
Valentine, C. D. et al., "Protein Trafficking Rates Assessed by Quantum Dot Quenching with Bromocresol Green", Traffic 2012, 13, pp. 25-29, John Wiley & Sons A/S.
Chauhan, V. P. et al., "Fluorescent Nanorods and Nanospheres for Real-Time In Vivo Probing of Nanoparticle Shape-Dependent Tumor Penetration**", Angew. Chem. Int. Ed. 2011, 50, pp. 11417-11420, iley-VCH Verlag GmbH & Co. KGaA, Weinheim.
Lane, L. A., "Physical Chemistry of Nanomedicine: Understanding the Complex Behaviors of Nanoparticles in Vivo", Annu. Rev. Phys. Chem. 2015, 66, pp. 521-547, Jan. 19, 2015.

(56) References Cited

OTHER PUBLICATIONS

Mazzier, D. et al., "Bulky toroidal and vesicular self-assembled nanostructures from fullerene end-capped rod-like polymers†", Chem. Commun., 2014, 50, pp. 4571-4574, The Royal Society of Chemistry.
Denisov, I. G. et al., "Cooperativity in Cytochrome P450 3A4 Linkages in Substrate Binding, Spin State, Uncoupling, and Product Formation*", J. Biol. Chem., vol. 282, No. 10, pp. 7066-7076, Mar. 9, 2007, The American Society for Biochemistry and Molecular Biology, Inc.
Li, Z. et al., "Size/Shape-Controlled Synthesis of Colloidal CdSe Quantum Disks: Ligand and Temperature Effects", J. Am. Chem. Soc., 2011, 133, pp. 6578-6586, ACS Publications.
Lim, S. J. et al., "Surface-Dependent, Ligand-Mediated Photochemical Etching of CdSe Nanoplatelets", J. Am. Chem. Soc. 2012, 134, pp. 7576-7579, ACS Publications.
Lim, S. J. et al., "Lipoprotein Nanoplatelets: Brightly Fluorescent, Zwitterionic Probes with Rapid Cellular Entry", J. Am. Chem. Soc., Dec. 19, 2015, 138, pp. 64-67, ACS Publications.
Yong, K. T. et al., "Quantum Rod Bioconjugates as Targeted Probes for Confocal and Two-Photon Fluorescence Imaging of Cancer Cells", Nano Letters, 2007, vol. 7, No. 3, pp. 761-765, ACS Publications.
Rowland, C. E. et al., "Picosecond energy transfer and multiexciton transfer outpaces Auger recombination in binary CdSe nanoplatelet solids", Nature Materials, vol. 14, May 2015, pp. 484-489, Macmillan Publishers Limited.
Roy, J. et al., "Direct Capture of Functional Proteins from Mammalian Plasma Membranes into Nanodiscs", Biochemistry 2015, 54, Sep. 28, 2015, pp. 6299-6302, ACS Publications.

\* cited by examiner

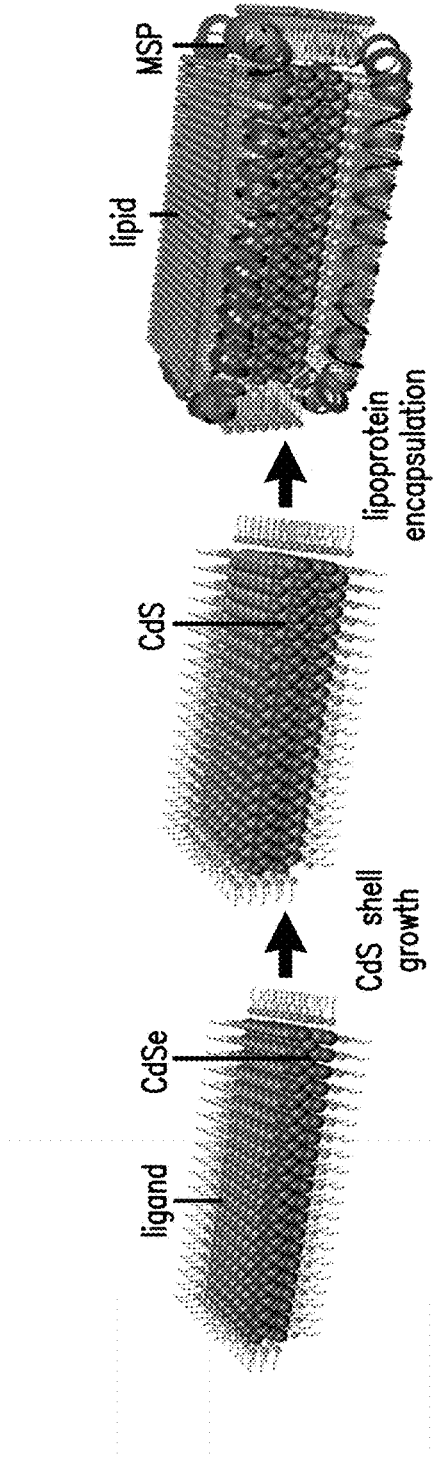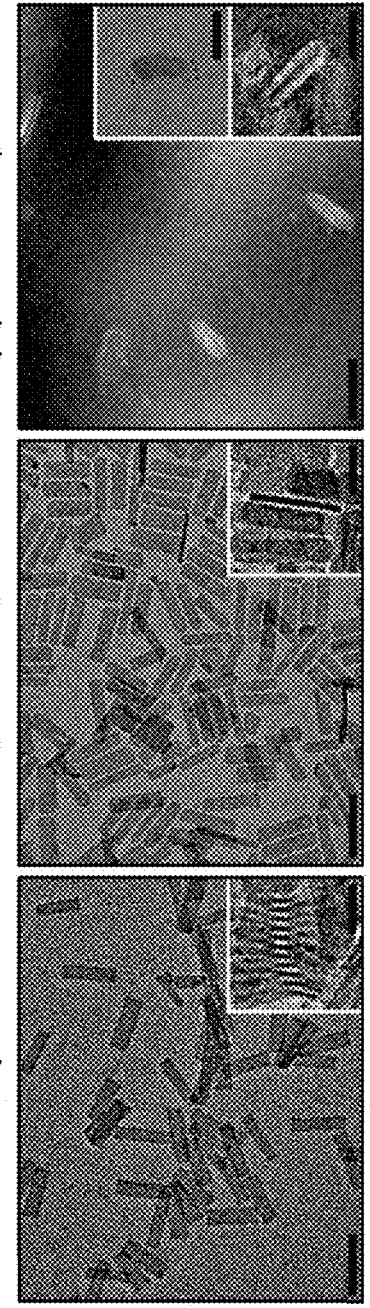
FIG. 1A
FIG. 1B
FIG. 1C
FIG. 1D

LIPOPROTEIN NANOPLATELETS: FLUORESCENT, ZWITTERIONIC PROBES FOR MOLECULAR AND CELLULAR IMAGING

RELATED APPLICATION

This application claims priority to U.S. Provisional Patent Application Ser. No. 62/209,257 filed on Aug. 24, 2015, the disclosure of which is incorporated by reference herein in its entirety.

FEDERAL FUNDING LEGEND

This invention was made with government support under CA153914 and NS087413 awarded by the National Institutes of Health. The government has certain rights in the invention.

BACKGROUND OF THE INVENTION

Semiconductor nanocrystals have recently been the subject of extensive multidisciplinary studies due to their unique physical, optical, and electronic properties.[1] Their major enabling property is bright and stable fluorescence emission that can be tuned across a broad range of wavelengths and excited with broadband light. This characteristic has enabled diverse applications as imaging agents and molecular probes in cells and tissues[1a] as well as light-emitting components of diodes and display devices.[1b,1c] These particles have become especially useful in single-molecule imaging applications where their unique combination of high photon emission rate and compact size have facilitated the discovery of a host of new biomolecular phenomena.[2]

The prototypical materials used in these applications are either quasi-spherical quantum dots (QDs) or elongated nanorods (NRs).[3] But recently a new class of semiconductor nanocrystal has emerged called a nanoplatelet (NPL) with a variety of unusual structural and optical properties.[3b,4] NPLs are thin crystalline sheets with atomically flat surfaces, tunable from 1.2 to 2.8 nm in thickness[4a,5] and roughly 5 to 700 nm in lateral dimensions,[6] and thus are colloidal analogues of quantum wells. A quantum well is a thin semiconductor layer which confines electrons and/or holes in the thin dimension of the layer surface, whereas the movement in the wide lateral dimensions is not restricted, The NPL fluorescence emission bandwidth is exceptionally narrow (8-20 nm full-width at half maximum, FWHM) compared to QDs (typically 25-35 nm FWHM) and organic fluorophores (typically 35-45 nm FWHM). The NPL light collecting efficiency can be very large; a single CdSe NPL with 1.5 nm thickness and 30 nm lateral dimensions has a molar extinction coefficient near $5 \times 10^7$ $M^{-1}$ $cm^{-1}$, roughly 1,000-times that of green fluorescent protein. In addition, unlike QDs, NPLs have high surface-area-to-volume ratios, which may allow both efficient transfer of energy and charge and efficient modulation of their optical properties by changes in their local environment. Together, these properties could allow multiplexed imaging with reduced spectral crosstalk as well as enhanced sensitivity for analyte detection. Recently CdSe-based NPLs have been coated with CdS shells resulting in greatly enhanced fluorescence quantum yields,[7] which is a critical step forward in the production of bright NPLs suitable for imaging in oxidizing environments.

However, it is an outstanding current challenge to stabilize NPLs in aqueous solutions compatible with cells and tissues. Like QDs and NRs, these materials are synthesized in organic solvents at high temperature, and the resulting colloids are coated with aliphatic ligands (e.g. oleic acid) that render them insoluble in polar solvents. With very large surface areas, we have found that conventional phase transfer techniques used for core/shell CdSe/CdS QDs, such as ligand exchange with hydrophilic thiolates, can damage the NPL structure and/or quench the fluorescence entirely.

SUMMARY OF THE INVENTION

Semiconductor nanoplatelets are planar nanocrystals that have attracted considerable attention due to their quantum well-like physics, atomically precise thickness, and unique photophysical properties such as narrow-band fluorescence emission. These attributes are of potential interest for applications in biomolecular and cellular imaging and sensing, but it has been challenging to colloidally stabilize these nanocrystals in biological media due to their large dimensions and tendency to aggregate. Here we introduce a new colloidal material that is a hybrid between a nanoplatelet and an organic nanodisc composed of phospholipids and lipoproteins. The phospholipids adsorb to flat surfaces on the nano-platelet and lipoproteins bind to sharp edges to enable monodisperse nanoplatelet encapsulation with long-term stability in biological buffers and high salt solutions. The lipoprotein-nanoplatelets are highly fluorescent with brightness comparable to wavelength-matched quantum dots at both the ensemble and single-molecule levels. They also exhibit a unique feature of rapid internalization into living cells, after which they retain their fluorescence. These unique properties suggest that lipoprotein-nanoplatelets are particularly well suited for applications in live-cell single-molecule imaging and multiplexed cellular labeling. The nanoparticles are also suitable for the explorations of the unknown behaviors of high aspect ratio materials, that is those materials having a high ratio of size differences in different dimensions, in living systems.

The invention provides a new class of water-stable nanoplatelets encapsulated in lipoproteins and lipids. Nanoplatelets are bright single-molecule emitters, like quantum dots, but with substantially narrower bandwidths. The nanoparticles retain their fluorescence after internalization in cells and thus are suitable for live-cell single-molecule imaging.

The invention provides NPLs that have been made colloidally stable by encapsulation in lipoproteins and lipids, and highly fluorescent nanoplatelets (NPLs) that are encapsulated in lipoproteins and lipids. Commercial applications include biomolecular imaging and sensing. Furthermore, these are the first example of NPLs that retain their fluorescence after internalization in cells, and thus are suitable for live-cell single-molecule imaging and explorations of the unknown behaviors of high aspect ratio materials in living systems.

The general methodology comprises:
1. Colloidal synthesis of CdSe core NPLs;
2. Layer-by-layer growth of a CdS shell (e.g. atomic layer deposition); and
3. Encapsulation of CdSe/CdScore/shell NPLs within components, e.g. encapsulation in lipids and lipoproteins through an evaporation-encapsulation process; efficient encapsulation of NPLs using zwitterionic phospholipids, detergents (sodium cholate or n-decyl-beta-maltoside), and amphipathic membrane scaffold proteins.

Regarding the second step, above, it is believed the shell grows only on the top and bottom of the NPL faces, and not around the edges, forming a sandwich. Therefore, the thickness increases, but the lateral dimensions do not change. This is an effect that results from the specific layer-by-layer shell growth process.

In one aspect the invention provides a composition comprising water-stable semi-conductor nanoplatelets (NPLs) encapsulated in an amphiphilic coating comprising phospholipids and lipoproteins.

In another aspect the invention provides a composition comprising lipoprotein-nanoplatelets (L-NPLs).

In embodiments:

the core and shell materials can comprise any compatible semiconductor material, most importantly the II-VI (e.g. CdSe), III-V (e.g. InP), the IV-VI (e.g. PbS), CIGS (e.g. CuInGaS), and IV (e.g. Si), and their alloys;

the phospholipids can have any number of carbons in their aliphatic lipid tails, generally 8, 10 or 12 to 28, 32 or 36, which can be saturated or unsaturated, and a variety of head groups such as ethanolamine, phosphocholine, PEG, etc.;

the lipoprotein can be of any compatible variety, such as membrane scaffold proteins or high density lipoproteins (HDLs), particularly helical, amphipathic membrane scaffold proteins (MSPs); and/or the phospholipid packing parameters yield flat structures and the lipoproteins stabilize truncated edges of the NPLs.

In aspects, the invention provides us of a subject composition for biomolecular imaging and sensing, or for live-cell single-molecule imaging.

In aspects, the invention provides methods of making a subject composition comprising: colloidal synthesis of NPL semiconductor cores; layer-by-layer growth of NPO semiconductor shells; and encapsulation of core/shell NPLs in lipid nanodisc components through an evaporation-encapsulation using zwitterionic phospholipids, detergents, and amphipathic lipoproteins.

The invention encompasses all combinations for particularly recited embodiments as though each combination had been separately and laboriously recited.

BRIEF DESCRIPTION OF THE DRAWINGS

FIG. 1. Synthesis and structure of lipoprotein-nanoplatelets. (FIG. 1A) Schematic illustration of synthesis steps. TEM (transmission electron microscope) images depict (FIG. 1B) CdSe core (unstained), (FIG. 1C) CdSe/CdS core/shell NPLs (unstained), and (FIG. 1D) L-NPL hybrids (counter-stained). Insets show side-views of the structures. Scale bars, 50 nm in wide-field images and 20 nm in insets.

FIG. 2. Optical properties of CdSe and CdSe/CdS L-NPLs (lipid nanoplatelets).

FIG. 3.

DETAILED DESCRIPTION OF THE INVENTION

Figure 2B:
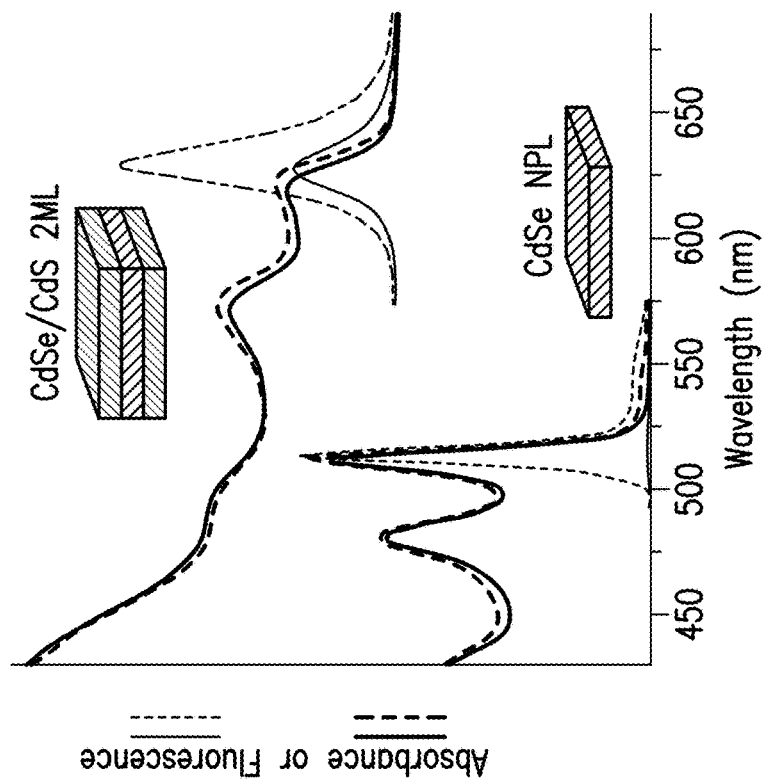
(FIG. 2B) Photographs of sample solutions under room light (left photo of each pair of photos) or 366-nm lamp excitation (right photo of each pair of photos) for NPLs in hexanes (photo pairs on left) and for L-NPLs in water (photo pairs on right).

The present invention relates to a lipoprotein nanoplatelet composition comprising semi-conductor nanoplatelets (NPLs) encapsulated in a hydrophilic coating further comprising lipids and lipoproteins.

The present invention also relates to a composition wherein the nanoplatelets are colloidally stable in aqueous solution. By colloidally stable is meant that the nanoplatelets are suspended or dispersed in the aqueous solution and do not demonstrate appreciable settling or agglomeration.

The present invention also relates to a composition wherein the lipid is a phospholipid. Phospholipids are a class of lipids that are a major component of all cell membranes. They can form lipid bilayers because of their amphiphilic characteristic. The structure of the phospholipid molecule generally consists of two hydrophobic fatty acid "tails" and a hydrophilic phosphate "head", joined together by a glycerol molecule.

The present invention also relates to a composition wherein the hydrophilic coating is a monolayer coating.

The present invention also relates to a composition, wherein the nanoplatelets comprise cores and shells, each of which cores and shells comprise a semiconductor material selected from groups II-VI, III-V, IV-VI, CIGS, and IV, and their alloys.

The present invention also relates to a composition wherein the nanoplatelets comprise a CdSe core.

The present invention also relates to a composition wherein the nanoplatelets comprise a CdS shell.

The present invention also relates to a composition wherein the nanoplatelets are in the general shape of a rectangular cuboid. Such a rectangular cuboid can have rough or smooth edges.

The present invention also relates to a composition wherein the nanoplatelets have a thickness from about 1 nm to about 7 nm, a length from about 5 nm to about 1000 nm, and a width of from about 5 nm to about 1000.

The present invention also relates to a composition wherein the nanoplatelets have a thickness from about 1 nm to about 7 nm, a length from about 10 nm to about 500 nm, and a width of from about 10 nm to about 200.

The present invention also relates to a composition wherein the nanoplatelets have a thickness from about 1.2 nm to about 2.8 nm, a length from about 5 nm to about 700 nm, and a width of from about 5 nm to about 700.

The present invention also relates to a composition wherein the nanoplatelets have a thickness of about 3 nm, a length of about 37 nm, and a width of about 10 nm.

The present invention also relates to a composition, wherein the nanoplatelets are in the general shape of a rectangular cuboid, wherein the nanoplatelets have a thickness of about 3 nm, a length of about 37 nm, and a width of about 10 nm have, are dimensioned to have two opposing (essentially, i.e. they are primarily) parallel planar surfaces defined as a top surface and a bottom surface, and two pairs of opposing (essentially, i.e. they are primarily) planar surfaces defining the edge surface of the cuboid, wherein the top and bottom surfaces are coated with a monolayer of about 1000 phospholipid molecules and the edge surface is coated with a monolayer of about 400 phospholipid molecules, and about 8 lipoproteins.

The present invention also relates to a composition wherein the CdSe core of the nanoplatelets has an extinction coefficient of about $2.4 \times 10^7$ cm$^{-1}$ M$^{-1}$ at 350 nm.

The present invention also relates to a composition wherein the nanoplatelets comprising a CdSe core and a CdS shell have an extinction coefficient of about $5.0 \times 10^7$ cm$^{-1}$ M$^{-1}$ at 350 nm.

The present invention also relates to a composition wherein the nanoplatelets comprising a CdSe core and a CdS shell have a fluorescence emission bandwidth of about 8 nm to about 20 nm full-width at half maximum.

The present invention also relates to a composition, wherein the phospholipids comprise aliphatic lipid tails of 8 to 36 carbons, which can be saturated or unsaturated, and head groups selected from ethanolamine, phosphocholine, and PEG.

The present invention also relates to a composition wherein the phospholipid is selected from 1,2-dimyristoyl-sn-glycero-3-phosphocholine (DMPC) and 1-palmitoyl-2-oleoyl-sn-glycero-3-phosphocholine (POPC).

The present invention also relates to a composition, wherein the lipoproteins are selected from membrane scaffold proteins and HDL.

The present invention also relates to a composition, wherein the lipoproteins comprise helical, amphipathic membrane scaffold proteins (MSPs).

The present invention also relates to a composition wherein the membrane scaffold protein is MSP1E3D1, which is a commercially available membrane scaffold protein 1E3D1 recombinant expressed in *E. coli*, from Sigma Aldrich.

The present invention also relates to a composition, wherein the nanoplatelets comprise cores and shells comprise semiconductor material selected from groups II-VI, III-V, IV-VI, CIGS, and IV, and their alloys;
the phospholipids comprise aliphatic lipid tails of 8 to 36 carbons, which can be saturated or unsaturated, and head groups selected from ethanolamine, phosphocholine, and PEG; and
the lipoproteins are selected from membrane scaffold proteins and HDL.

The present invention also relates to a composition wherein the phospholipid packing parameters yield flat structures and the lipoproteins stabilize truncated edges of the nanoplatelets.

The present invention also relates to a composition comprising lipoprotein-nanoplatelets.

The present invention also relates to the use of a lipoprotein nanoplatelet composition for biomolecular imaging and sensing.

The present invention also relates to the use of a lipoprotein nanoplatelet composition for live-cell single-molecule imaging.

The present invention also relates to a method of making a lipoprotein nanoplatelet composition, comprising:
colloidal synthesis of NPL semiconductor cores;
layer-by-layer growth of NPL semiconductor shells; and
encapsulation of core/shell NPLs in lipid hydrophilic coating components through an evaporation-encapsulation using zwitterionic phospholipids, detergents, and amphipathic lipoproteins.

The present invention also relates to a method of making a lipoprotein nanoplatelet composition wherein the hydrophilic coating components comprise phospholipids and lipoproteins,
wherein the phospholipid is selected from 1,2-dimyristoyl-sn-glycero-3-phosphocholine (DMPC) and 1-palmitoyl-2-oleoyl-sn-glycero-3-phosphocholine (POPC) and the lipoprotein is selected from the membrane scaffold protein MSP1E3D1,
wherein the phospholipids (DMPC or POPC) are dispersed in CHCl$_3$ and added in a 10,000:1 phospholipid:nanoplatelet molar ratio,
and wherein the MSP1E3D1 is added in a 100:1 MSP1E3D1:nanoplatelet molar ratio.

Lipoprotein Nanoplatelets

Here we demonstrate the production of a new class of water-stable NPLs encapsulated by monolayers of lipids and lipoproteins through micelle-like self-assembly. These lipoprotein-nanoplatelets (L-NPLs) are hybrids of lipoprotein nanodiscs, which are colloidal analogues of plasma membranes made of a phospholipid bilayer stabilized by helical, amphipathic membrane scaffold proteins (MSPs) that encircle the nanodisc like a belt.[8]

Analogous structures have previously been used to solubilize integral and transmembrane proteins in aqueous solution and encapsulate hydrophobic drugs[8c,9], and lipid-encapsulation has been shown to transform hydrophobic colloidal nanoparticles into biocompatible nanostructures.[10] However, it is critical to geometrically match the nanoparticle morphology with the native self-assembled lipid structure in order to yield stable and individually-coated nanoparticles. For example, spherical nanoparticles such as QDs and gold colloids have been successfully encapsulated by amphiphilic polymers,[10] polyethylene glycol (PEG)-containing phospholipids[11] and globular lipoproteins[12] that individually self-assemble as spherical colloids in aqueous solution. This is due to a high volume ratio of the polar head domain to the nonpolar tail domain, or a large packing parameter, which matches the high surface curvature of the encapsulated isotropic particles.[13] Lipids with small packing parameters do not efficiently encapsulate individual spherical nanoparticles, but instead form large liposomes entrapping multiple nanoparticles.[14] We hypothesized that nanodisc components, which include phospholipids with packing parameters that yield flat structures and MSPs that stabilize the truncated edges with high curvature, might be effective for encapsulation of flat NPLs.

L-NPLs were synthesized in a three step process schematically depicted in FIG. 1A, comprising (1) colloidal synthesis of CdSe core NPLs, (2) layer-by-layer growth of a CdS shell, and (3) encapsulation of CdSe/CdS core/shell NPLs within a lipid/lipoprotein coating. CdSe was used as the core material due to robust syntheses that allow independent tuning of lateral dimensions and thickness, as well as narrow-band fluorescence emission in the visible spectrum.[4a,5a] FIG. 1B shows an example structure of uniform rectangular-shaped CdSe NPLs with 41 nm×11 nm lateral dimensions and 1.8 nm thickness, as measured by transmission electron microscopy (TEM). These thin nanocrystals are flexible and were observed to form stacks of twisted NPLs (see inset). Effective layer-by-layer shell growth techniques were recently introduced for deposition of CdS on CdSe, which has a wider bandgap (2.5 eV) than the core CdSe material (1.76 eV).[7] The shell boosts quantum yield and allows better preservation of fluorescence in biological media (see below). The shell was grown by colloidal atomic layer deposition (cALD), as reported by Talapin and coworkers.[7a] FIG. 1C shows that after 2 monolayers of growth, the lateral dimensions were similar (42 nm×12 nm), but the thickness increased to 3.0 nm. Twisted and stacked NPLs were no longer observed via TEM (see inset) indicating that shell growth increased structural rigidity. Finally, these core/shell NPLs were encapsulated in lipid nanodisc components through an evaporation-encapsulation process previously used to solubilize membrane proteins.[8c] The counter-stained TEM images in FIG. 1D show individual core/shell NPLs uniformly surrounded by a 3-4 nm organic shell, confirming successful formation of L-NPLs. The thickness of the coating was similar to that of typical lipid bilayers that, in the present material system, should be composed of an inner layer of oleate ligands bound to the NPL surface and an outer layer of phospholipids and membrane scaffold proteins (MSPs). These images were obtained after extensive purification to remove empty nanodiscs.

Efficient encapsulation of NPLs required three components: phospholipids, detergents, and MSPs. To generate L-NPLs, NPLs were dispersed in chloroform and self-assembled with an excess of phospholipids through slow solvent evaporation followed by dispersion in phosphate buffered saline (PBS) containing a mixture of detergents (sodium cholate or n-decyl-beta-maltoside) and amphipathic MSPs, (e.g. MSP1E3D1, which is a commercially available membrane scaffold protein 1E3D1 recombinant expressed in *E. coli*, from Sigma Aldrich). Zwitterionic phospholipids were used to minimize nonspecific interactions with cells, and were chosen to have a packing parameter near 1 to allow dense assembly on the flat NPL surfaces; we used 1,2-dimyristoyl-sn-glycero-3-phosphocholine (DMPC) or 1-palmitoyl-2-oleoyl-sn-glycero-3-phosphocholine (POPC). Eliminating any one of the three components significantly reduced both the phase transfer efficiency and stability of NPLs in aqueous solution. Phospholipids alone natively self-assemble into larger liposomal structures,[15] yielding a low percentage of NPLs transfer into aqueous buffer and most of the products were insoluble aggregates. Detergents dissociate liposomal structures into smaller metastable micelles;[15a] this increased the phase transfer efficiency of NPLs but aggregation was still substantial. With the addition of MSPs, NPLs were readily dispersed in water without substantial aggregates, yielding of encapsulated NPLs that were stable for more than one month after extensive dialysis and density gradient centrifugation in high salt (even >4 M NaCl) to remove empty nanodiscs and expel associated detergents. MSPs also eliminated fluorescence quenching effects of detergents that may strip off oleate ligands from the NPL surface.

We characterized L-NPLs using multiple analytical methods and determined that the structure is consistent with the schematic in FIG. 1A, in which lipids cover flat NPL surfaces and MSP proteins adsorb to sharp edges. For L-NPLs made from NPLs with average dimensions of 37 nm×10 nm×3 nm, it was determined that there was an average of 1,193 DMPC lipids per NPL based on elemental analysis of cadmium (which is only in the CdSe/CdS NPL core) and phosphorous (only in the phospholipid). Assuming that DMPC adopts a similar area as in nanodiscs (0.69 nm2 DMPC-1),[8b] this quantity is consistent with a monolayer coating of the flat top and bottom of the NPL (740 nm$^2$ surface area, or 1,070 lipids) and some of the sides (282 nm$^2$ surface area, or 409 lipids). The slight deficiency is likely covered by MSP proteins. We calculated an average of 7.7 MSPs per L-NPL by spectral analysis of L-NPLs prepared with dye-labeled MSP. MSPs possibly localize to edges to interact with lipid tail sides where they reside analogously in nanodiscs. This is consistent geometrically, as MSP1E3D1 extends to a length of 38 nm in a nano-disc (circumference of a nanodisc with 13 nm diameter),[8b] so theoretically at least 5.0 MSPs are needed to cover both top and bottom edges of the NPL (total perimeter length of 188 nm), only slightly less than the measured value of 7.7. Deviations can arise from protein conformation differences on the circular nanodisc versus the rectangular NPL. This model was further justified by an imaging study to localize MSPs using TEM. We conjugated gold colloids activated with N-hydroxysuccinimide (NHS) to L-NPLs. Because only the MSP protein contains primary amines with which NHS will conjugate, gold should only localize to the protein. TEM showed that NHS-gold was almost exclusively localized around the L-NPL perimeter, as opposed to the particle center (see FIG. 1D inset).

Figure 2A:
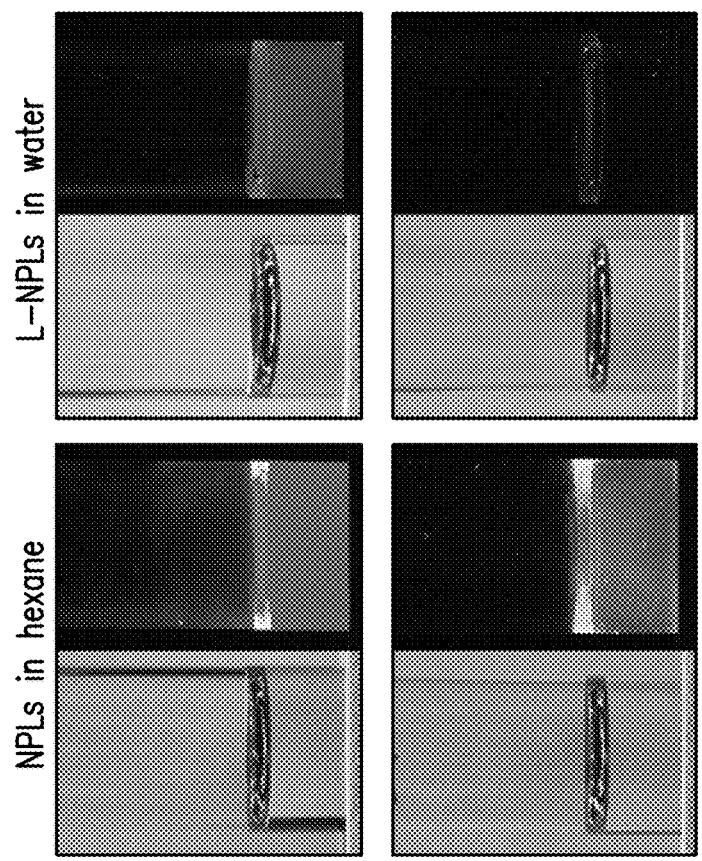
(FIG. 2A) Ultraviolet-visible absorption (absorbance) (heavy-weight solid and dotted lines) and fluorescence (light-weight solid and dotted lines) spectra of CdSe core (bottom) and CdSe/CdS core/shell NPLs (top) in hexane (dotted lines) and corresponding L-NPL structures in PBS (solid lines).

The optical properties of NPLs and L-NPLs composed of CdSe core and CdSe/CdS core/shell structures are shown in FIG. 2. The crystalline CdS shell was necessary for maintaining fluorescence in water after nanodisc encapsulation, as the core-only NPLs were completely non-fluorescent after nanodisc-encapsulation, despite a quantum yield (QY) of 2.3% in organic solvents. With CdS shell growth, the QY increased significantly in organic solvents, and could reach up to 80% with thick shells (7-8 ML).[7c] Unlike the core-only NPLs, the fluorescence of core/shell NPLs was preserved after nanodisc encapsulation, but the QY partially decreased in a manner that depended on the CdS shell thickness. For a 2-ML shell (the structure used in cells below) a 4.3% QY in hexane resulted in a 1.6% QY in water. Thinner shells yielded a more substantial QY reduction while thicker shells provided greater QY retention. While a shell is necessary to maintain fluorescence, increasing thickness attenuates the more unique optical attributes of these materials as well as their potential for environmental sensitivity and flexibility. For example, CdSe-only NPLs have exceptionally narrow emission bands (FWHM=9 nm for $\lambda_{em}$=515 nm), but they monotonically broaden with shell growth, possibly due to increasing structural heterogeneity or/and increased electron-phonon coupling.[7c] We find that with an intermediate shell thickness (2-3 ML), bands were still much more narrow (FWHM=21 nm at $\lambda_{em}$=626 nm) than those of spectrally-matched QDs (FWHM=25-35 nm at $\lambda_{em}$=600-650 nm), so we focused on this structural set for further development.

Figure 3B:
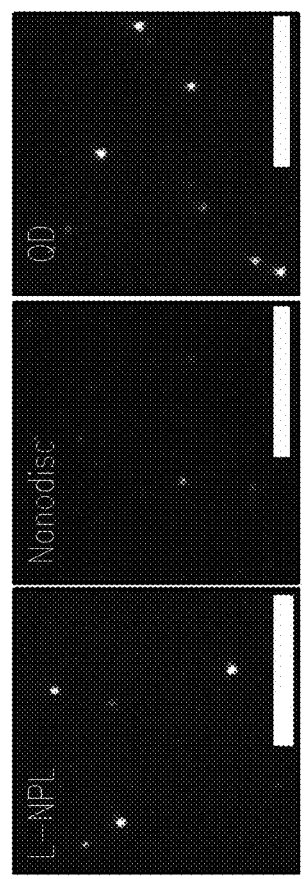
(FIG. 3B) Zeta potential measurements in phosphate buffered solution indicated that all nanoparticles were anionic; the L-NPLs and nanodiscs were similar (−25 to −30 mV) but the zwitterionic QDs, which had no protein component, had a lower charge (−11 mV).
Figure 3A:
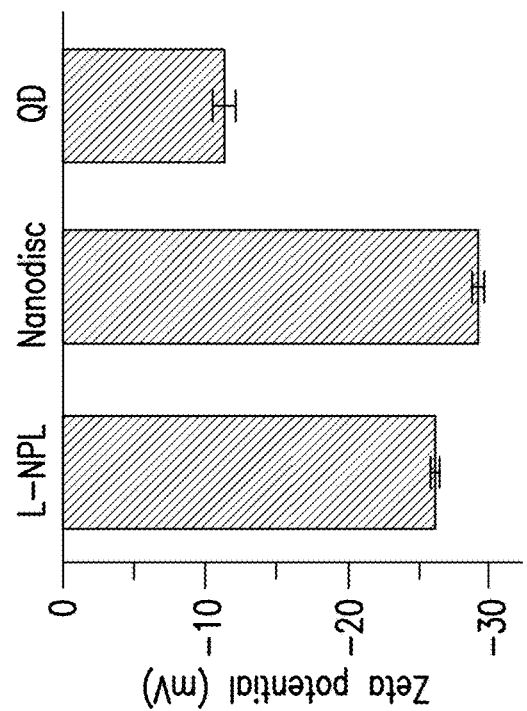
(FIG. 3A) Single-particle fluorescence images of red L-NPLs (left), dye-labeled nanodiscs (center) and red water-dispersed QDs (right).
Figures 3C, 3D, 3E:
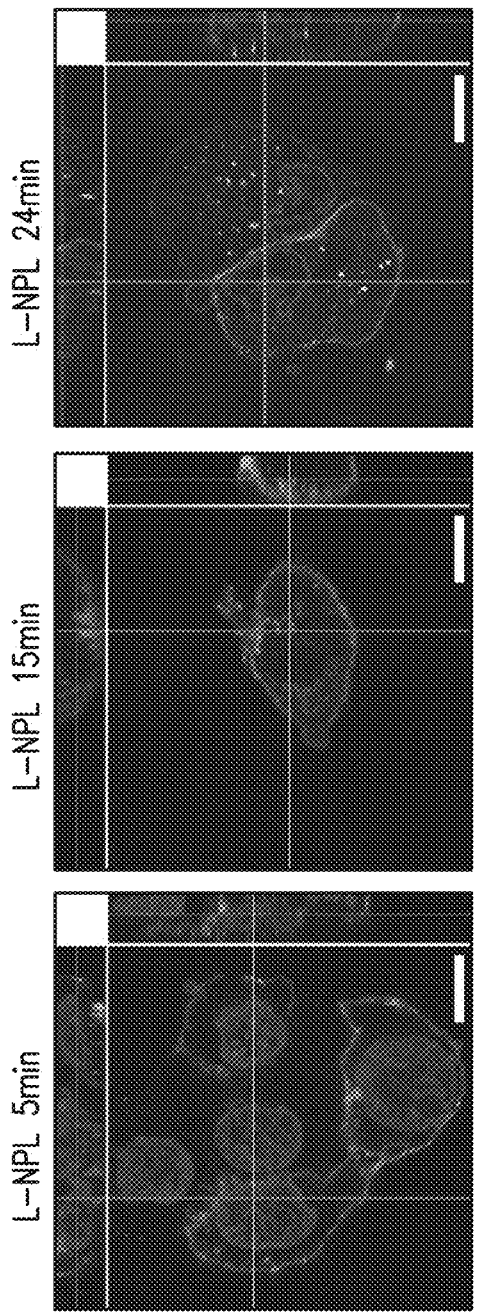
(FIGS. 3C-3H) Confocal microscopy fluorescence images showing fluorescence from L-NPLs (red) internalized in A431 cells. When added to cells at equal particle concentrations (1 nM), cells exposed to L-NPLs showed a much higher level of intracellular red fluorescence (FIGS. 3C, 3D, and 3E) compared to control cells and cells exposed to nanodiscs or QDs (FIGS. 3F, 3G, and 3H).

To investigate the potential of L-NPLs as fluorescent imaging probes, we measured their optical and diffusive behavior at the single-particle level using epifluorescence and total internal reflectance fluorescence (TIRF) microscopy with 488 nm laser excitation. L-NPLs and QDs with similar emission wavelengths were spin-coating from dilute aqueous solutions on a glass coverslip. Individual emitters were readily detected as distinguished by fluorescence intermittency (blinking) and homogeneous intensity levels in the blinking "on" state. L-NPLs exhibiting significantly longer "off"-times and shorter "on"-times (see example in FIGS. 3A and 3B). The "on"-time fluorescence brightness values were measured for at least 250 single particles, using the method of Lagerholm and coworkers.[16] As depicted in FIG. 3C, the average relative single-particle brightness values of L-NPLs ($B_{rel,sp}$=2.06±0.98) and QDs ($B_{rel,sp}$=1.94±0.90) were similar, with L-NPLs having slightly higher brightness (by 6%). In comparison, absolute brightness values at the ensemble level were calculated from the relation $B_{rel}$=QY·ε, where ε the extinction coefficient calculated based on the sample core volume per particle from TEM and the $CdSe_xS_{1-x}$ concentration derived from elemental analysis.[17] Ensemble brightness values were similar for L-NPLs ($B_{rel,en}$=4.0×10$^5$ cm$^{-1}$ M$^{-1}$) and QDs ($B_{rel,en}$=4.7×10$^5$ cm$^{-1}$ M$^{-1}$), with L-NPLs being slightly dimmer (by 14%). The small mismatch between the ensemble and the single-particle brightness values may originate from error in extinction coefficient calculations of L-NPLs due to their anisotropic structure, the possible presence of "dark" L-NPLs that would not be counted in the single-particle analysis, or preferential alignment on the glass substrate. These results confirmed that L-NPLs are bright single-molecule emitters, comparable to QDs, but with substantially narrower bandwidths.

The diffusion of L-NPLs was probed through single-particle fluorescence imaging in dilute glycerol-water mixtures. By fitting the mean squared displacements of 429 single particle trajectories to a model of Brownian motion, the mean center-of-mass diffusion coefficient was calculated to be $1.55\pm0.71$ $\mu m^2$ $s^{-1}$ in 50% (w/w) glycerol-sodium borate buffer (see FIG. 3D). By the Stokes-Einstein equation, the correlated diameter for an equivalent sphere is 46.1 nm, which is close to many QDs in common use.[18]

Figures 3F, 3G, 3H:
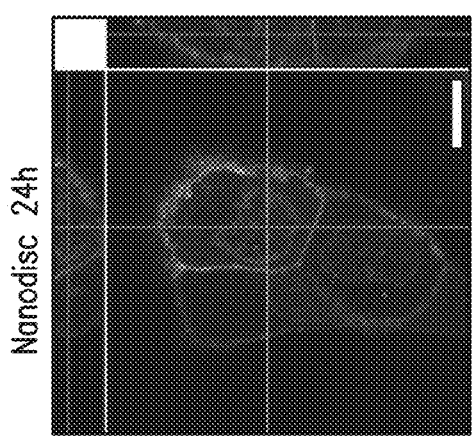

We also investigated the interaction of L-NPLs with living A431 human epidermoid carcinoma cells to evaluate their use as single-molecule cellular imaging probes and cellular labels (see FIGS. 3E-3G).

L-NPLs did not readily stick to the surfaces of cells in phosphate buffered saline, consistent with their zwitterion-inc surface chemistry. After several hours, internalization of the L-NPLs was evident, and the internalized NPLs remained fluorescent inside cells after 24 hours, as verified by quenching extracellular nanoparticles using bromocresol green and imaging focal planes away from the substrate surface (see FIG. 3G).[19]

We compared L-NPLs directly with two chemically analogous nanoparticles: nanodiscs composed of the same lipid/lipoprotein components labeled with a fluorophore (Texas Red) and zwitterionic QDs. All three had similar red emission wavelengths and were readily visible at the single-particle level under identical imaging conditions (FIG. 3A). Zeta potential measurements in phosphate buffered solution indicated that all nanoparticles were anionic; the L-NPLs and nanodiscs were similar (−25 to −30 mV) but the zwitterionic QDs, which had no protein component, had a lower charge (−11 mV) (FIG. 3B). When added to cells at equal particle concentrations (1 nM), cells exposed to L-NPLs showed a much higher level of intracellular red fluorescence (FIGS. 3C, 3D, and 3E) compared to control cells and cells exposed to nanodiscs or QDs (FIGS. 3F, 3G, and 3H). We tracked this via confocal microscopy and stained cells with a nuclear dye (blue) and a plasma membrane dye (green). We observed that internalization is rapid, with L-NPLs colocalizing with the membrane within 5 minutes of exposure, and becoming internalized within 15 minutes. After 24 hours, uptake was substantial, consisting of bright punctate cytosolic spots of L-NPLs likely in endosomal vesicles. It is surprising that among three chemically similar particles, only L-NPLs exhibited substantial uptake. Zwitterionic components were shared by all particles, so they likely did not contribute. It is possible that MSP protein was also not likely the contributor, since MSP-containing nanodiscs did not exhibit substantial uptake. A protein conformation change is also not likely the source, as the result was similar when MSP was PEGylated to block protein-mediated cell association. The strong uptake can arise from the high surface area and low curvature of L-NPLs, for which multiple weak adsorption events can become substantial in strength through multivalency. Overall these observations suggest that L-NPLs are a promising class of fluorophore for intracellular imaging and for efficient fluorescence tagging of cells. These observations reveal that L-NPLs provide a useful class of fluorophore for imaging cells at the single-molecule level.

We have engineered new composite nanocrystals comprising a quantum well-like nanoplatelet encapsulated within phospholipid and lipoprotein components of a nanodisc, yielding colloidally stable fluorophores with bright emission at the ensemble and single particle levels. The unique shapes and optical properties of these materials are useful in the context of single-molecule imaging, optical cellular tagging, and drug delivery, as high aspect ratio particles have been observed to have enhanced permeation through crowded tissues and unique delivery capabilities in living animals. This new material composite can reveal, at the single-particle level, how 2-dimensional materials interact with biological systems. These studies exemplify the use of a colloidal fluorescent quantum well employed in biological systems. These findings of rapid cellular entry suggest that these materials can be useful for cellular labeling applications for highly multiplexed spectral encoding of cellular identity.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Example 1—Materials

Materials for Nanoplatelet Synthesis

Cadmium oxide (CdO, 99.99+%), cadmium acetate hydrate ($Cd(Ac)_2.H_2O$, 99.99+%), selenium powder (Se, ~100 mesh, 99.99%), ammonium sulfide (($NH_4)_2S$, 40-48 wt. % in $H_2O$), tetramethylammonium hydroxide solution (TMAH, 25 wt. % in methanol), 3-mercaptopropionic acid (MPA, >99%), tributylphosphine (TBP, 97%), sodium chloride (NaCl), bromocresol green (ACS Reagent, dye content 95%), and dimethyl sulfoxide (DMSO, >99.9%, anhydrous) were purchased from Sigma-Aldrich. 1-octadecene (ODE, 90% tech.), oleic acid (OAc, 90% tech.), and oleylamine (OLA, 80-90% C18-content) were purchased from Acros Organics. Tris base (99%) and hydrochloric acid (37% in water) were purchased from Fisher Scientific. N-methylformamide (NMF, >99%) was obtained from Tokyo Chemical Industry. Other solvents including chloroform, hexane, methanol, ethanol, ethyl acetate, acetone, phosphate buffered sailine (PBS) were purchased from various suppliers including Acros Organics, Fisher Scientific, and Macron Fine Chemicals.

Materials for Polymeric Ligand Synthesis

Tris(carboxyethyl)phosphine (TCEP, 98%), polyacrylic acid (PAA, MW 1.8 kDa), dimethylethylenediamine (DMDA, 99%), N,N-diisopropylethylamine (DIPEA, 99.5%), N,N,N'N'-tetramethyl-o-(1H-benzotriazol-1-yl)uronium hexafluorophosphate (HBTU, 98%), 1-hydroxybenzotriazole hydrate (HOBt, 97%), 1,3-propanesultone (98%), trifluoroacetic acid (TFA, 99%), phenol (99%), triisopropylsilane (TIPS, 98%) were purchased from Sigma-Aldrich. Dimethylformamide (DMF, 99.8% anhydrous) was purchased from Alfa Aesar. All chemicals were used as received. S-trityl-protected cysteamine was prepared according to the literature.[21]

Materials for Lipoprotein Coatings, Labeling, and Surface Modification

The phospholipids 1,2-dimyristoyl-sn-glycero-3-phosphocholine (DMPC) and 1-palmitoyl-2-oleoyl-sn-glycero-3-phosphocholine (POPC) were purchased from Avanti Polar Lipids. Decyl maltoside (C10M) and ultrapure sodium cholate (≥97%) was purchased from Affymetrix.

Membrane scaffold protein (MSP1E3D1) was expressed and purified as described (see Denivos et al.).[22] Texas Red® 1,2-dihexadecanoyl-sn-glycero-3-phosphoethanolamine, triethylammonium salt (Texas Red® DHPE) and Alexa Fluor® 680 NHS ester, bis(triethylammonium salt) (Alexa Fluor® 680 NHS) were obtained from ThermoFisher Scientific. Mono-Sulfo-NHS-Nanogold® (d ~1.4 nm) was purchased from Nanoprobes. α-Methoxy-ω-NHS ester (PEG-NHS, 2 kDa) was purchased from Rapp Polymere.

Materials for Negative Staining TEM

Sodium phosphotungstate hydrate (PTA, >99.9%) was purchased from Sigma-Aldrich.

Example 2—Zwitterionic Polymer Synthesis

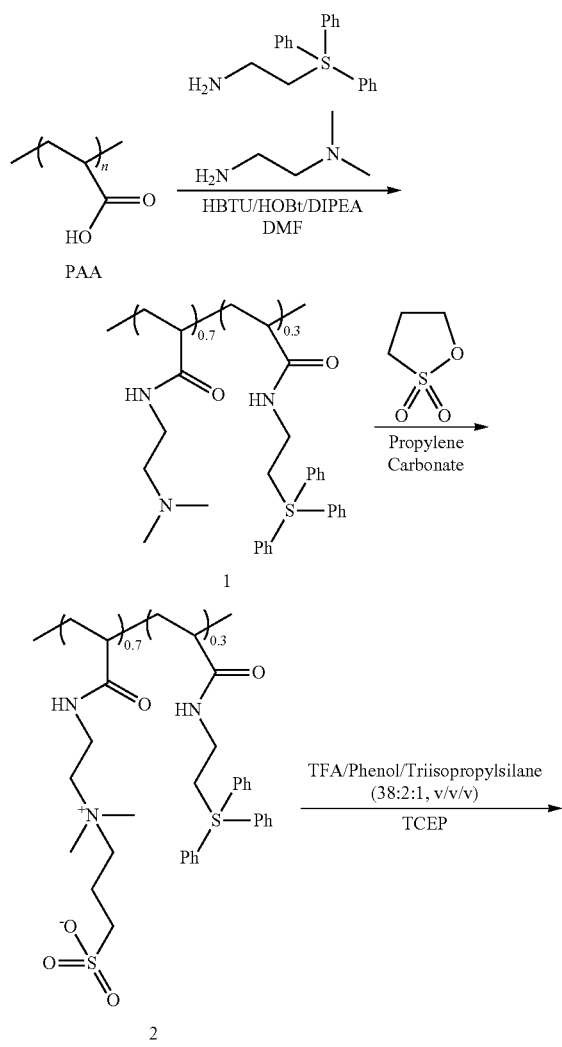
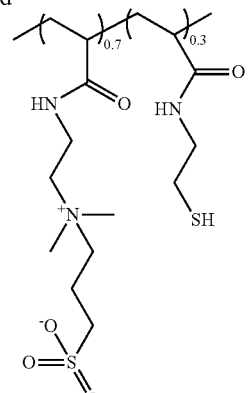

Polymer 1

PAA (116.67 mg, 1.62 mmol COOH), HBTU (910.17 mg, 2.4 mmol), HOBt (356.98 mg, 2.31 mmol) were dissolved in DMF (5 mL). DIPEA (846 μL, 4.8 mmol) was added to activate the carboxylic acid and 10 minutes later S-trityl-protected cysteamine (181.8 mg, 0.57 mmol) and DMDA (120 μL, 1.1 mmol) were added. The mixture was stirred overnight at room temperature. The product was precipitated with the addition of 10 mM NaOH solution (250 mL) and collected by centrifugation. The product was redissolved in acetone, mixed with anhydrous $Na_2SO_4$, filtered, and dried under vacuum. The viscous oil was washed with ether to remove any residual solvent to yield the product 1 as a yellow powder. Yield: 40%. 1H NMR ($d_6$-DMSO, δ, ppm, 500 MHz): 7.1-7.4 (Ar—H, br), 3.25-3.6 (br), 2.84 (—S—$CH_2$, br), 2.75 and 2.4 (—$CH_2$—N<, m), 2.0-2.4 ($CH_3$, br).

Polymer 2

1 (100 mg, 0.7 mmol) was treated with 1,3-propanesultone (129 mg, 1.05 mmol) in dry propylene carbonate (1.5 mL) under continuous stirring for 24 hours at room temperature, followed by 24 hours at 80° C. The product 2 was precipitated from the reaction mixture with ether (40 mL) to obtain a white powder. The product was then rinsed with ether and dried under vacuum. Yield: 70%. $^1$H NMR ($D_2O$, δ, ppm, 500 MHz): 6.5-7.51 (Ar—H, br), 3.25-3.75 (br), 3.0-3.2 (br), 2.4-3.0 (br), 1.8-2.3 (br).

Poly(Thiol and Sulfobetaine) (PTSB)

2 (10 mg, 11 μmol SH) and TCEP (3.2 mg, 11 μmol) was treated with TFA/phenol/TIPS (38:2:1 v/v/v, 1 mL) under $N_2$ for 5 hours. The solid PTSB product was precipitated with ether (10 mL) and collected by centrifugation at 7,000 g/5 min.

Example 3—Nanoplatelet (NPL) Synthesis

Core CdSe NPL

CdSe NPLs were synthesized and purified using literature methods with slight modifications.[23] In a typical synthesis, CdO (0.6 mmol), OAc (1.2 mmol), and ODE (15 mL) were mixed in a 50-mL round bottom flask (r.b.f.) and heated to ~200° C. under nitrogen until the mixture became clear and colorless due to the formation of cadmium oleate. The solution was cooled to 140° C. and Se powder (0.6 mmol) was added. Then the temperature was quickly raised to 240° C. at a rate of ~20° C./min. At 190° C., Cd(Ac)$_2$ (0.6 mmol) was swiftly added into the mixture to initiate NPL growth. After reaching 240° C., the mixture was heated for an additional 10 min and the reaction was quenched by removing the heating mantle. When cooled to ~130° C., OAc (1 mL) was added to stabilize the NPL dispersion. The reaction yielded a mixture of NPLs with the first exciton $\lambda_{abs}$ at 510 nm as well as quantum dots (QDs). For purification, the reaction mixture was diluted with hexane (~15 mL), divided into two 50-mL centrifuge tubes, and sonicated for ~5 min before adding ethanol (~30 mL) containing TBP (1 mL) into each tube and centrifuged at 7,000 g for 5 min to precipitated all nanocrystals (NPLs and QDs). Precipitates were redispersed in hexane (20 mL per tube) with sonication, then only NPLs were precipitated by adding ethanol (5 mL per tube) and centrifuging. Finally, pure NPLs were redispersed in hexane and stored as a stock solution.

Core/Shell CdSe/CdS NPLs

CdS shells were grown layer-by-layer on purified CdSe NPLs by following the colloidal atomic layer deposition protocol developed by Ithurria and Talapin[23c] with slight modifications. In a typical reaction, a biphasic mixture of CdSe NPLs in hexane (top phase; band edge absorbance ~4, 2 mL) and NMF (bottom phase; 2 mL) was prepared in a glass vial with magnetic stir bar. While gently stirring the mixture, a drop of $(NH_4)_2S$ solution (20 µL) was added into the top phase. This induced a sudden color change from yellow to dark orange followed by the flocculation of NPLs due to the deposition of sulfide layer on the NPL surface. The aggregates were eventually homogeneously dispersed into the bottom NMF phase. After complete phase transfer in 1-2 min, the top phase was discarded and the bottom phase was washed with hexane twice. The NPLs were isolated from excess sulfide ions by precipitation with ethyl acetate and centrifugation at 7,000 g for 5 min Sulfide-coated NPLs were redispersed in pure NMF (2 mL) and a solution of $Cd(Ac)_2$ in NMF (0.1 M, 50 µL) was added, which induced a color change to dark red due to the growth of a monolayer (ML) of CdS shell on the NPL surface. After a few minutes, NPLs were isolated from the excess Cd ions by precipitation with ethyl acetate. These NPLs were redispersed in NMF and an additional monolayer of CdS shell was grown through another cycle of $(NH_4)_2S$ addition—precipitation—redispersion in NMF—$Cd(Ac)_2$ addition—precipitation—redispersion in NMF. The final core/shell NPLs were transferred back to organic phase by adding OAc (~100 µL) and OLA (~100 µL) in a biphasic mixture of NPL solution in NMF (bottom phase) and hexane (top phase; 2 mL) while gently stirring the mixture for ~10 min. After complete phase transfer, the bottom phase was discarded and the NPLs were purified by precipitation with excess methanol. Finally, pure core/shell NPLs were dispersed in $CHCl_3$ and stored in the dark until use.

Example 4—Lipoprotein-Nanoplatelet (L-NPL) Preparation and Purification

L-NPL Assembly

In a typical synthesis, a CdSe/CdS core/shell NPL stock in $CHCl_3$ (~100 nM, $\varepsilon_{350\,nm}$ ~5×10$^7$ cm$^{-1}$ M$^{-1}$, 1 mL) was sonicated for 10 min and phospholipids (DMPC or POPC) dispersed in $CHCl_3$ were added in a 10,000:1 lipid:NPL molar ratio. The mixture was sonicated for 10 min and $CHCl_3$ was evaporated under a steady stream of $N_2$. The dry product was stored under vacuum to ensure complete $CHCl_3$ removal. The NPL-phospholipid mixture was reconstituted in PBS or Tris (0.1M, pH 7.4) containing detergents (sodium cholate or C10M) (10 mM, 1 mL) and sonicated for 10 min before rocking at 22° C. for 30 min. Next, MSP (MSP1E3D1) was added in a 100:1 MSP:NPL molar ratio and the mixture was rocked at 22° C. for 6-8 hours to form a macromolecular assembly between the NPL, phospholipids, and MSPs, yielding L-NPL hybrids as well as a large excess of empty nanodiscs. The as-prepared L-NPL hybrid solution was filtered through a syringe filter (0.2 µm pores) to remove any aggregates, then the clear dispersion was dialyzed in the same buffer (PBS or Tris) for 1 day using a 50 kDa molecular weight cutoff (MWCO) dialysis tube (Spectrum Laboratories, Inc.) to remove excess lipids and detergents and concentrated using a 50 kDa MWCO centrifugal filter (Amicon® Ultra, EMD Millipore). Excess nanodiscs remaining after dialysis were removed using density gradient centrifugation.

NaCl Density Gradient Centrifugation

A saturated NaCl solution (~6.5 M, d=1.20 g/mL, 10 mL) was prepared by dissolving NaCl in distilled water at room temperature. A series of lower density solutions (d=1.17, 1.14, 1.10, 1.07, and 1.03 g/mL) were prepared by diluting the saturated NaCl stock. In a 14-mL ultracentrifugation tube (Ultra-Clear™, Beckman Instruments, Inc.), a NaCl density gradient medium was prepared by carefully stacking NaCl layers with successively decreasing densities (~1 mL per layer). This discontinuous density gradient medium was then centrifuged at 26,000 g for 20 min to form a continuous density gradient medium. Then, 0.1-0.2 mL of concentrated L-NPL stock was loaded on top of the density gradient medium and centrifuged at 26,000 g for 2 hours. The denser L-NPLs migrated into the medium whereas the lighter nanodiscs remained at the top of the medium. After ultracentrifugation, the location of L-NPLs was identified by the absorption color (brown) and the fluorescence under UV light (red). The portion of medium containing L-NPLs was recovered and dialyzed (50 kDa membrane, in PBS or Tris) to remove excess NaCl.

Example 5—Dye-Labeled Lipoprotein and Nanodisc Synthesis

Dye-Labeled MSP

For quantification of MSP number per L-NPL, Alexa Fluor® 680-labeled MSP was prepared using amine-reactive Alexa Fluor® 680 NHS. A solution of the dye in anhydrous DMSO was added dropwise to a stirring solution of MSPE3D1 (50 uM) in 0.1 M sodium carbonate buffer (pH 8.3). The dye:MSP1E3D1 molar ratio was 10:1. The reaction was stirred at room temperature for 4 hours and the protein product was purified using a G-25 column (GE Healthcare). The number of dyes per MSP was measured spectroscopically by absorbance of MSP at 280 nm ($\varepsilon$=29,400 cm$^{-1}$ M$^{-1}$) and absorbance of the dye at 683 nm ($\varepsilon$=184,000 cm$^{-1}$ M$^{-1}$).

Dye-Labeled Nanodiscs

Dye-labeled nanodiscs were prepared by incorporating a dye-labeled lipid during synthesis using previously described methodology.[24] Briefly, Texas Red® 1,2-Dihexadecanoyl-sn-Glycero-3-Phosphoethanolamine (DHPE) and DMPC were suspended in a solution of cholate (50 mM) in potassium phosphate buffer (KPi, pH 7.4) at a 3:97 molar ratio and sonicated for 5 min. Next, these phospholipids were added to MSP1E3D1 at a 130:1 lipid:MSP molar ratio and equilibrated for 30 min. Assembly of the Texas Red® DHPE-containing nanodiscs was initiated upon addition of Amberlite Biobeads for detergent removal and the mixture was gently rocked overnight at 22° C. Biobeads were removed and the homogenous labeled nanodiscs were purified using size exclusion chromatography with a Superdex 200 10/300 column (GE Healthcare) coupled to an HPLC (Waters Alliance 2695), running 100 mM KPi (pH 7.4)

buffer at a 0.5 mL/min flow. Collected fractions of fluorescent nanodiscs were pooled and concentrated using Amicon Ultra (10,000 MWCO) centrifugal filters (Millipore).

Example 6—L-NPL Labeling and PEGylation

L-NPLs with Dye-Labeled MSP

L-NPLs were prepared and purified by following the steps described in 1d using dye-labeled MSPs prepared in 1e instead of normal (unlabeled) MSPs. The average number of MSPs per L-NPLs was determined based on the relative absorbance contributions from the dye and NPL.

Nanogold-Labeled L-NPLs

A purified L-NPL solution in PBS (~1.45 nM, 1 mL) was mixed with a freshly prepared solution of Mono-Sulfo-NHS-Nanogold® in PBS at a 500:1 nanogold:L-NPL ratio. The mixture was incubated for 1 hour at room temperature, then excess nanogold was removed by multiple cycles of centrifugal filtration using a 100 kDa MWCO filter (Amicon® Ultra, EMD Millipore). As a negative control, purified L-NPLs were mixed with non-functional nanogold prepared by quenching Mono-Sulfo-NHS-Nanogold® with Tris ($10^5$ molar excess) for 12 hours.

L-NPL PEGylation

A purified L-NPL dispersion in PBS (~1 nM, 0.5 mL) was mixed with PEG-NHS in DMSO (0.625 mM, 50 µL) and incubated at room temperature for 2 hours. Excess PEG and DMSO were removed by multiple cycles of centrifugal filtration using a 50 kDa MWCO filter.

Example 7—Polymer-Coated QDs

Zwitterionic PTSB-Coated QDs

Purified red-emitting QDs ($\lambda_{em}$ 600 nm) in hexane were phase transferred into NMF by adding TMAH (100 equivalents of QD surface atoms). PTSB dissolved in NMF (0.5 mL) was mixed with the OH$^-$-coated QDs in NMF (1 µM, 0.4 mL) (5:1 thiol to QD surface atom) and purged with $N_2$ for 2 min. The mixture was stirred at 110° C. for 4 hours and then diluted with 50 mM sodium borate buffer (pH 8.5, 4 mL). QDs were purified using centrifugal filtration (Amicon Ultra 50 kDa MWCO) in 50 mM sodium borate buffer (pH 8.5). The dilution-filtration cycle was performed five times.

Example 8—Single-Molecule Imaging, Diffusion, and Cell Interaction Studies

For single-molecule brightness and blinking analysis, a dilute suspension of L-NPLs or QDs in PBS (~4 µM for L-NPLs and ~100 µM for QDs, 100 µL) was spin-coated on a glass coverslip (2,500 rpm, 30 s) and a solution of dye-labeled nanodisc (1 nM, 100 µL) was drop-and-dried on a coverslip to achieve similar particle density. Then fluorescence was immediately measured under ambient conditions using a Zeiss epifluorescence/total internal reflectance fluorescence (TIRF) microscope. To determine brightness values from single-particle fluorescence videos, the method of Arnspang et al. was used.[16] The center positions (x,y) of emitting spots were determined using the detection/estimation/deflation algorithm of Serge et al.[25] and the intensities of 3×3 points centered on these spots were measured. Intensity histograms were then plotted for each emitter, which were fit to a sum of a symmetric Gaussian function (the background signal) and an asymmetric Gaussian function (the emitter signal) using the least squares method. These two Gaussian centroid positions were compiled into histograms for each particle sample and plotted. Because the emission wavelengths of the NPLs and QDs were similar, no scaling factor was needed to account for the wavelength dependent sensitivity of the detector.

For single-molecule diffusion studies, 0.5 nM L-NPLs were dispersed in a 50% (w/w) mixture of glycerol and aqueous sodium borate buffer (50 mM, pH 8.5). 100 µL of this solution was then transferred to a #1.5 coverglass and imaged using highly inclined and laminated optical sheet (HILO) microscopy. Emitter position centroids were determined using the methods of Serge et al.[25] to calculate mean squared displacements per time increment. The first 3-5 points from MSD plots were fitted to a line with slope equal to 2 D, where D is the diffusion coefficient.

For cell interaction studies, A431 cells (ATCC) were seeded at a density of 30,000-35,000 cells/cm$^2$ in CellView glass dishes (Greiner Bio-One) 24 hours before incubation with nanoparticles (1 nM) in phenol red-free serum-free DMEM (Cell Media Facility, UIUC). Incubation was allowed to proceed for 5 min, 15 min, 1 hour, or 24 hours at 37° C. After the respective incubation times, the cells were rinsed with PBS three times in order to remove free nanoparticles. The cells were then stained sequentially with 3,3'-dioctadecyloxacarbocyanine perchlorate (DiO) (Santa Cruz Biotechnology) to label the membrane (10 min at 37° C.) and Hoechst 33258 (Life Technologies) to label the nuclei (15 min at 4° C.). After staining, the cells were fixed using paraformaldehyde (electron Microscopy Sciences) freshly diluted to 4% in PBS for 10 min at room temperature.

To study the effect of L-NPL surface PEGylation on cellular uptake, A431 cells (ATCC) were seeded at a density of 30,00-35,000 cells/cm$^2$ in CellView glass dishes (Greiner Bio-One, Kremsmünster, Austria) 24 hours before addition of nanoparticles (0.076 nM) in phenol red-free serum-free DMEM (Cell Media Facility, UIUC). Incubation was allowed to proceed for 24 h at 37° C. The cells were then rinsed with PBS three times in order to remove the free nanoparticles, and then stained and fixed using the same procedures described above.

Example 9—Instrumentation

Optical Spectroscopy and Fluorescence Quantum Yield (QY) Measurements

Absorption spectra were obtained with an Agilent Cary 5000 UV-Vis-NIR spectrometer and fluorescence spectra were acquired using a Horiba NanoLog spectrofluorometer. For fluorescence QY measurements, the solution was diluted to give NPL absorption of ~0.1 at 490 nm QY was calculated relative to a reference dye (fluorescein in 1 mM NaOH, QY=92%).

Transmission Electron Microscopy (TEM)

TEM images were obtained using a JEOL 2010 LaB$_6$ high-resolution microscope in the Frederick Seitz Materials Research Laboratory Central Research Facilities at University of Illinois. For NPLs in organic solvents, samples were prepared by placing a drop of dilute NPL solution in hexane on an ultrathin carbon film TEM grid (Ted Pella; Product #01824) and then wicking the solution off with a tissue. For L-NPLs, a drop of sample solution in buffer was added to the grid and allowed to incubate for 5 min before wicking off the liquid with a tissue. Then a drop of 1% PTA solution in DI water (pH 7) was loaded and wicked off after 30-40 s.

Elemental Analysis and NPL Extinction Coefficient Calculation

Elemental analysis was performed using a PerkinElmer Optima 2000DV ICP-optical emission spectrometer. Detailed protocols for sample preparation and NPL extinction coefficient calculation can be found in our other work (Lim).[26] The extinction coefficient of the CdSe core NPL (37 nm×10 nm×1.8 nm) was 2.4×10$^7$ cm$^{-1}$ M$^{-1}$ at 350 nm. The extinction coefficient of the CdSe/CdS core/shell NPL (37 nm×10 nm×3.0 nm) was 5.0×10$^7$ cm$^{-1}$ M$^{-1}$ at 350 nm.

$^1$H NMR $^1$H NMR spectra were recorded using a Varian U500 MHz or VXR-500 MHz spectrometer.

Zeta Potential

For zeta potential measurements, a sample dispersion (L-NPLs, nanodiscs, or QDs) in high-salt buffer (e.g. PBS) was dialyzed against phosphate buffer (10 mM, pH 7.4) for 1 day. Zeta potential was measured using a Malvern Zetasizer.

Ultracentrifugation

For density gradient centrifugation of L-NPL samples, ultracentrifugation was performed using a Beckman Coulter Optima™ L-90K Ultracentrifuge equipped with a SW 40 Ti swinging bucket rotor.

Fluorescence Microscopy

For single molecule imaging and diffusion studies, samples were imaged via wide-field illumination on a Zeiss Axio Observer.Z1 inverted microscope with a 100×1.45 NA alpha Plan-Fluar oil immersion microscope objective with excitation from a 488 nm/100 mW OPSL laser set in epifluorescence excitation mode. Excitation light was filtered using a 482/18 laser-line bandpass filter (Semrock Inc., Rochester, N.Y.), and emission light was filtered with a 624/40 bandpass filter (Semrock Inc.). Images were acquired using a Photometrics eXcelon Evolve 512 EMCCD using Zeiss Zen software. Single molecule imaging was performed with epi-illumination of the sample and diffusion studies were performed using a HILO angle. Single-molecule brightness movies were collected at a rate of ~16 frames/s, while diffusion coefficient measurement movies were collected at a rate of ~7.6 frames/s.

For cell interaction studies, fixed cell samples were imaged using a Zeiss LSM 700 confocal microscope with a 63×/1.40 NA oil immersion objective at the Core Facilities at the Carl R. Woese Institute for Genomic Biology. The L-NPLs, QDs, and fluorescent nanodiscs were excited using a 555-nm laser line, DiO was excited using a 488-nm laser line, and Hoechst was excited with a 405-nm laser line. Z-stacks of all three channels were acquired with slice spacing of ~0.74 μm spanning the entire height of the cell or cell cluster.

REFERENCES (1) (a) Kairdolf, B. A.; Smith, A. M.; Stokes, T. H.; Wang, M. D.; Young, A. N.; Nie, S. *Ann. Rev. Anal. Chem.* 2013, 6, 143. (b) Talapin, D. V.; Lee, J. S.; Kovalenko, M. V.; Shevchenko, E. V. *Chem. Rev.* 2010, 110, 389. (c) Mashford, B. S.; Stevenson, M.; Popovic, Z.; Hamilton, C.; Zhou, Z.; Breen, C.; Steckel, J.; Bulovic, V.; Bawendi, M.; Coe-Sullivan, S.; Kazlas, P. T. *Nat. Photon.* 2013, 7, 407.

(2) (a) Zahid, M. U.; Smith, A. M. In *Optical Nanoscopy and Novel Microscopy Techniques*; Xi, P., Ed.; CRC Press: 2014. (b) Pinaud, F.; Clarke, S.; Sittner, A.; Dahan, M. *Nat. Methods* 2010, 7, 275.

(3) (a) Smith, A. M.; Nie, S. *Acc. Chem. Res.* 2010, 43, 190. (b) Lim, S. J.; Smith, A.; Nie, S. *Curr. Opin. Chem. Eng.* 2014, 4, 137. (c) Deka, S.; Quarta, A.; Lupo, M. G.; Falqui, A.; Boninelli, S.; Giannini, C.; Morello, G.; De Giorgi, M.; Lanzani, G.; Spinella, C.; Cingolani, R.; Pellegrino, T.; Manna, L. *J. Am. Chem. Soc.* 2009, 131, 2948.

(4) (a) Ithurria, S.; Tessier, M. D.; Mahler, B.; Lobo, R.; Dubertret, B.; Efros, A. *Nat. Mater.* 2011, 10, 936. (b) Bouet, C.; Tessier, M. D.; Ithurria, S.; Mahler, B.; Nadal, B.; Dubertret, B. *Chem. Mater.* 2013, 25, 1262.

(5) (a) Ithurria, S.; Dubertret, B. *J. Am. Chem. Soc.* 2008, 130, 16504. (b) Son, J. S.; Wen, X.-D.; Joo, J.; Chae, J.; Baek, S.-i.; Park, K.; Kim, J H.; An, K.; Yu, J. H.; Kwon, S. G.; Choi, S.-H.; Wang, Z.; Kim, Y.-W.; Kuk, Y.; Hoffmann, R.; Hyeon, T. *Angew. Chemi Int. Ed.* 2009, 48, 6861.

(6) Bouet, C.; Mahler, B.; Nadal, B.; Abecassis, B.; Tessier, M. D.; Ithurria, S.; Xu, X. Z.; Dubertret, B. *Chem. Mater.* 2013, 25, 639.

(7) (a) Ithurria, S.; Talapin, D. V. *J. Am. Chem. Soc.* 2012, 134, 18585. (b) Mahler, B.; Nadal, B.; Bouet, C.; Patriarche, G.; Dubertret, B. *J. Am. Chem. Soc.* 2012, 134, 18591. (c) Tessier, M. D.; Mahler, B.; Nadal, B.; Heuclin, H.; Pedetti, S.; Dubertret, B. *Nano Lett.* 2013, 13, 3321.

(8) (a) Bayburt, T. H.; Grinkova, Y. V.; Sligar, S. G. *Nano Lett.* 2002, 2, 853. (b) Denisov, I. G.; Grinkova, Y. V.; Lazarides, A. A.; Sligar, S. G. *J. Am. Chem. Soc.* 2004, 126, 3477. (c) Bayburt, T. H.; Sligar, S. G. *FEBS Lett.* 2010, 584, 1721.

(9) (a) Bayburt, T. H.; Grinkova, Y. V.; Sligar, S. G. *Arch. Biochem. Biophys.* 2006, 450, 215. (b) Das, A.; Zhao, J.; Schatz, G. C.; Sligar, S. G.; Van Duyne, R. P. *Anal. Chem.* 2009, 81, 3754. (c) McDougle, D. R.; Palaria, A.; Magnetta, E.; Meling, D. D.; Das, A. *Prot. Sci.* 2013, 22, 964.

(10) (a) Pellegrino, T.; Manna, L.; Kudera, S.; Liedl, T.; Koktysh, D.; Rogach, A. L.; Keller, S.; Radler, J.; Natile, G.; Parak, W. J. *Nano Lett.* 2004, 4, 703. (b) Smith, A. M.; Nie, S. M. *Angew. Chemie Int. Ed.* 2008, 47, 9916.

(11) (a) Dubertret, B.; Skourides, P.; Norris, D. J.; Noireaux, V.; Brivanlou, A. H.; Libchaber, A. *Science* 2002, 298, 1759. (b) Mulder, W. J. M.; Koole, R.; Brandwijk, R. J.; Storm, G.; Chin, P. T. K.; Strijkers, G. J.; de Mello Donegá, C.; Nicolay, K.; Griffioen, A. W. *Nano Lett.* 2005, 6, 1.

(12) (a) Cormode, D. P.; Skajaa, T.; van Schooneveld, M. M.; Koole, R.; Jarzyna, P.; Lobatto, M. E.; Calcagno, C.; Barazza, A.; Gordon, R. E.; Zanzonico, P.; Fisher, E. A.; Fayad, Z. A.; Mulder, W. J. M. *Nano Lett.* 2008, 8, 3715. (b) Skajaa, T.; Zhao, Y.; van den Heuvel, D. J.; Gerritsen, H. C.; Cormode, D. P.; Koole, R.; van Schooneveld, M. M.; Post, J. A.; Fisher, E. A.; Fayad, Z. A.; de Mello Donega, C.; Meijerink, A.; Mulder, W. J. M. *Nano Lett.* 2010, 10, 5131. (c) McMahon, K. M.; Mutharasan, R. K.; Tripathy, S.; Veliceasa, D.; Bobeica, M.; Shumaker, D. K.; Luthi, A. J.; Helfand, B. T.; Ardehali, H.; Mirkin, C. A.; Volpert, O.; Thaxton, C. S. *Nano Lett.* 2011, 11, 1208.

(13) Israelachvili, J. N. *Intermolecular and Surface Forces, 3rd Edition*; Academic Press: Boston, Mass., 2011.

(14) (a) Gopalakrishnan, G.; Danelon, C.; Izewska, P.; Prummer, M.; Bolinger, P.-Y.; Geissbühler, I.; Demurtas, D.; Dubochet, J.; Vogel, H. *Angew. Chemie Int. Ed.* 2006, 45, 5478. (b) Al-Jamal, W. T.; Al-Jamal, K. T.; Tian, B.; Lacerda, L.; Bomans, P. H.; Frederik, P. M.; Kostarelos, K. *ACS Nano* 2008, 2, 408. (c) Zheng, W.; Liu, Y.; West, A.; Schuler, E. E.; Yehl, K.; Dyer, R. B.; Kindt, J. T.; Salaita, K. *J. Am. Chem. Soc.* 2014, 136, 1992.

(15) (a) Johnsson, M.; Edwards, K. *Biophys. J.* 2003, 85, 3839. (b) Nagarajan, R. *Langmuir* 2002, 18, 31.

(16) Arnspang, E. C.; Brewer, J. R.; Lagerholm, B. C. *PLoS ONE* 2012, 7, e48521.

(17) Jasieniak, J.; Smith, L.; Embden, J. v.; Mulvaney, P.; Califano, M. *The J. Phys. Chem. C* 2009, 113, 19468.

(18) Smith, A. M.; Nie, S. M. *Nat. Biotechnol.* 2009, 27, 732.

(19) Valentine, C. D.; Verkman, A. S.; Haggie, P. M. *Traffic* 2012, 13, 25.

(20) (a) Chauhan, V. P.; Popovic, Z.; Chen, O.; Cui, J.; Fukumura, D.; Bawendi, M. G.; Jain, R. K. *Angew. Chem. Int. Ed.* 2011, 50, 11417. (b) Lane, L. A.; Qian, X. M.; Smith, A. M.; Nie, S. *Annu. Rev. Phys. Chem.* 2015, 66, 521.

(21) Mazzier, D.; Mba, M.; Zerbetto, M.; Moretto, A. *Chem. Commun.* 2014, 50, 4571.

(22) Denivos, I. G.; Baas, B. J.; Grinkova, Y. V.; Sligar, S. G. *J. Biol. Chem.* 2007, 282, 7066.

(23) (a) Li, Z.; Peng, X. *J. Am. Chem. Soc.* 2011, 133, 6578. (b) Lim, S. J.; Kim, W.; Shin, S. K. *J. Am. Chem. Soc.* 2012, 134, 7576. (c) Ithurria, S.; Talapin, D. V. *J. Am. Chem. Soc.* 2012, 134, 18585.

(24) McDougle, D. R.; Baylon, J. L.; Meling, D. D.; Kambalyal, A.; Grinkova, Y. V.; Hammernik, J.; Tajkhorshid, E.; Das, A. *Biochim. Biophys. Acta.* 2015, 1848, 2460.

(25) Serge, A.; Bertaux, N.; Rigneault, H.; Marguet, D. *Nat. Methods.* 2008, 5, 687.

(26) Lim, S. J.; Zahid, M. U.; Le, P.; Ma, L.; Entenberg, D.; Harney, A. S.; Condeelis, J.; Smith, A. M. *Nat. Commun.* 2015, 6, 8210.

Also:

Lim, S. J. et al., J. Am. Chem. Soc., 2016, 138, 64-67.

Yong, K. T.; Qian, J.; Roy, I.; Lee, H. H.; Bergey, E. J.; Tramposch, K. M.; He, S. L.; Swi-hart, M. T.; Maitra, A.; Prasad, P. N. Nano Lett. 2007, 7, 761.

Rowland, C. E.; Fedin, I.; Zhang, H.; Gray, S. K.; Govorov, A. O.; Ta-lapin, D. V.; Schaller, R. D. Nat. Mater. 2015, 14, 484.

Roy, J.; Pondenis, H.; Fan, T. M.; Das, A. Biochemistry 2015, 54, 6299.

Skajaa, T.; Zhao, Y.; van den Heuvel, D. J.; Gerritsen, H. C.; Cor-mode, D. P.; Koole, R.; van Schooneveld, M. M.; Post, J. A.; Fisher, E. A.; Fayad, Z. A.; de Mello Donega, C.; Meijerink, A.; Mulder, W. J. M. Nano Lett. 2010, 10, 5131.

McMahon, K. M.; Mutharasan, R. K.; Tripathy, S.; Veliceasa, D.; Bobeica, M.; Shumaker, D. K.; Luthi, A. J.; Helfand, B. T.; Ardehali, H.; Mirkin, C. A.; Volpert, O.; Thaxton, C. S. Nano Lett. 2011, 11, 1208.

Unless otherwise explained, all technical and scientific terms used herein have the same meaning as commonly understood by one of ordinary skill in the art to which a disclosed disclosure belongs. The singular terms "a," "an," and "the" include plural referents unless context clearly indicates otherwise. Similarly, the word "or" is intended to include "and" unless the context clearly indicates otherwise. All references cited herein are incorporated by reference.

While the present disclosure can take many different forms, for the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications of the described embodiments, and any further applications of the principles of the disclosure as described herein are contemplated as would normally occur to one skilled in the art to which the disclosure relates.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein.

All patents and publications mentioned in the specification are indicative of the levels of skill of those skilled in the art to which the disclosure pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are disclosed, it should be understood that compounds known and available in the art prior to Applicant's disclosure, including compounds for which an enabling disclosure is provided in the references cited herein, are not intended to be included in the composition of matter aspects herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the disclosure without resort to undue experimentation. All art-known functional equivalents, of any such materials and methods are intended to be included in this disclosure. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended aspects.

Although the present disclosure has been described with reference to certain embodiments thereof, other embodiments are possible without departing from the present disclosure. The spirit and scope of the appended aspects should not be limited, therefore, to the description of the preferred embodiments contained herein. All embodiments that come within the meaning of the aspects, either literally or by equivalence, are intended to be embraced therein. Furthermore, the advantages described above are not necessarily the only advantages of the disclosure, and it is not necessarily expected that all of the described advantages will be achieved with every embodiment of the disclosure.

What is claimed is:

1. A method for making a lipoprotein nanoplatelet (NPL) composition comprising:
   colloidal synthesis of NPL semiconductor cores;
   layer-by-layer growth of NPL semiconductor shells; and
   encapsulation of core/shell NPLs in lipid hydrophilic coating components through an evaporation-encapsulation using zwitterionic phospholipids, detergents, and amphipathic lipoproteins,
   wherein the hydrophilic coating components comprise phospholipids and lipoproteins,
   wherein the phospholipid is selected from 1,2-dimyristoyl-sn-glycero-3-phosphocholine (DMPC) and 1-palmitoyl-2-oleoyl-sn-glycero-3-phosphocholine (POPC) and the lipoprotein is the membrane scaffold protein MSP1E3D1,
   wherein the phospholipids DMPC or (POPC) are dispersed in $CHCl_3$ and added in a 10,000:1 phospholipid:nanoplatelet molar ratio,
   and wherein the MSP1E3D1 is added in a 100:1 MSP1E3D1:nanoplatelet molar ratio.

2. A method according to claim 1 wherein the nanoplatelets are colloidally dispersed in an aqueous solution.

3. A method according to claim 1 wherein the hydrophilic coating is a monolayer coating.

4. The method of claim 1, wherein the cores and shells comprise a semiconductor material selected from groups II-VI, III-V, IV-VI, I-III-VI$_2$, and IV, and their alloys.

5. The method of claim 4, wherein the nanoplatelets comprise a CdSe core.

6. The method of claim 5, wherein the nanoplatelets comprise a CdS shell.

7. The method of claim 1 wherein the nanoplatelets are in the general shape of a rectangular cuboid.

8. The method of claim 7, wherein the nanoplatelets have a thickness from about 1 nm to about 7 nm, a length from about 5 nm to about 1000 nm, and a width of from about 5 nm to about 1000.

9. The method of claim 7, wherein the nanoplatelets have a thickness from about 1 nm to about 7 nm, a length from about 10 nm to about 500 nm, and a width of from about 10 nm to about 200.

10. The method of claim 7, wherein the nanoplatelets have a thickness from about 1.2 nm to about 2.8 nm, a length from about 5 nm to about 700 nm, and a width of from about 5 nm to about 700.

11. The method of claim 7, wherein the nanoplatelets have a thickness of about 3 nm, a length of about 37 nm, and a width of about 10 nm.

12. The method of claim 1, wherein the nanoplatelets are in the general shape of a rectangular cuboid,
   wherein the nanoplatelets have a thickness of about 3 nm, a length of about 37 nm, and a width of about 10 nm have,
   are dimensioned to have two opposing parallel planar surfaces defined as a top surface and a bottom surface, and two pairs of opposing planar surfaces defining the edge surface of the cuboid,
   wherein the top and bottom surfaces are coated with a monolayer of about 1000 phospholipid molecules and the edge surface is coated with a monolayer of about 400 phospholipid molecules, and about 8 lipoproteins.

13. The method of claim 1 wherein the phospholipids cover the the top and bottom surfaces and the lipoproteins are adsorbed to the edges of the nanoplatelets.

* * * * *